(12) United States Patent
Mangold et al.

(10) Patent No.: US 11,701,471 B2
(45) Date of Patent: Jul. 18, 2023

(54) PACKAGING HAVING SLIDING LAYER AND METHOD FOR PHARMACEUTICAL AND COSMETIC SUBSTANCES AND PREPARATION FOR PRODUCING SAME

(71) Applicant: SCHOTT Pharma AG & Co. KGaA, Mainz (DE)

(72) Inventors: Stephanie Mangold, Schornsheim (DE); Tamara Sweeck, Bad Kreuznach (DE)

(73) Assignee: SCHOTT Pharma AG & Co. KGaA, Mainz (DE)

( * ) Notice: Subject to any disclaimer, the term of this patent is extended or adjusted under 35 U.S.C. 154(b) by 766 days.

(21) Appl. No.: 16/564,928

(22) Filed: Sep. 9, 2019

(65) Prior Publication Data

US 2020/0078523 A1   Mar. 12, 2020

(30) Foreign Application Priority Data

Sep. 10, 2018   (DE) .................. 10 2018 122 001.4

(51) Int. Cl.
*A61M 5/31*   (2006.01)
*C10M 107/50*   (2006.01)
(Continued)

(52) U.S. Cl.
CPC ........ *A61M 5/3134* (2013.01); *C10M 107/50* (2013.01); *A61M 2005/3131* (2013.01); *A61M 2205/0222* (2013.01); *A61M 2205/0238* (2013.01); *A61M 2207/00* (2013.01); *C10M 2227/045* (2013.01); *C10M 2229/025* (2013.01);
(Continued)

(58) Field of Classification Search
CPC ........ A61M 5/3134; A61M 2005/3131; A61M 2205/0222; A61M 2205/0238; A61M 5/3129; C10M 107/50; C10M 2227/045; C10M 2229/025; C10N 2040/50
See application file for complete search history.

(56) References Cited

U.S. PATENT DOCUMENTS 4,061,609 A   12/1977   Bobear
4,767,414 A    8/1988   Williams et al.
(Continued)

FOREIGN PATENT DOCUMENTS

EP   0 920 879 B1   4/2003

OTHER PUBLICATIONS

Chinese Office Action dated Oct. 8, 2021 for Chinese Application No. 201910851365.8 (12 pages).
(Continued)

*Primary Examiner* — Ellen M McAvoy
(74) *Attorney, Agent, or Firm* — Taylor IP, P.C

(57) ABSTRACT

A liquid preparation for application to an inner side of a hollow body to produce a sliding layer on a packaging for pharmaceuticals or cosmetic products comprises the following constituents: a reactive silicone system for forming a silicone network of the sliding layer, a catalyst for catalyzing the cross-linking reaction of the reactive silicone system, at least one unreactive silicone oil, and at least one diluent. The diluent comprises a silicon-containing compound and a content of the at least one diluent in the preparation amounts to more than 45 percent by weight and less than 95 percent by weight in the preparation.

19 Claims, 4 Drawing Sheets

(51) Int. Cl.
    *C10N 40/00* (2006.01)
    *C10N 50/08* (2006.01)
(52) U.S. Cl.
    CPC ...... *C10N 2040/50* (2020.05); *C10N 2050/08* (2013.01)

(56) References Cited

U.S. PATENT DOCUMENTS

| | | | |
|---|---|---|---|
| 6,296,893 B2 | 10/2001 | Schott | |
| 10,066,182 B2* | 9/2018 | Santucci-Aribert | B05D 3/068 |
| 10,441,947 B2 | 10/2019 | Ou | |
| 10,925,927 B2 | 2/2021 | Brockmeyer et al. | |
| 11,331,434 B2 | 5/2022 | Vogt | |
| 2001/0004466 A1 | 6/2001 | Heinz et al. | |
| 2002/0012741 A1 | 1/2002 | Heinz et al. | |
| 2004/0050152 A1 | 3/2004 | King | |
| 2007/0228669 A1* | 10/2007 | Liu | A61L 27/165 |
| | | | 525/478 |
| 2007/0287954 A1* | 12/2007 | Zhao | C09D 183/04 |
| | | | 604/93.01 |
| 2008/0071228 A1 | 3/2008 | Wu et al. | |
| 2010/0266856 A1 | 10/2010 | White et al. | |
| 2012/0143148 A1 | 6/2012 | Zhao et al. | |
| 2013/0030380 A1* | 1/2013 | Abe | A61M 5/31513 |
| | | | 604/265 |
| 2013/0122314 A1* | 5/2013 | Ou | A61L 29/14 |
| | | | 427/2.12 |
| 2013/0190695 A1 | 7/2013 | Wu | |
| 2014/0031764 A1* | 1/2014 | Abe | A61L 29/14 |
| | | | 604/221 |
| 2016/0348025 A1* | 12/2016 | Ou | C10M 139/06 |
| 2018/0117220 A1* | 5/2018 | Yatabe | C09D 183/08 |
| 2018/0237659 A1* | 8/2018 | Kim | C09D 183/04 |
| 2020/0172740 A1* | 6/2020 | Ou | C09D 7/62 |

OTHER PUBLICATIONS

German Office Action dated Apr. 16, 2019 for German Application No. 10 2018 122 001.4 (10 pages).
German Office Action dated Oct. 30, 2019 for German Application No. 10 2018 122 001.4 (10 pages).
"Momentive LSR Topcoat A", Material Safety Date Sheet dated Feb. 18, 2009 (8 pages).
"Momentive LSR Topcoat", Technical Data Sheet dated Mar. 13, 2018 (3 pages).
Extended European Search Report dated Mar. 13, 2020 for European Application No. 19 19 6347 (7 pages).
Chinese Office Action dated Jun. 30, 2022 for Chinese Application No. 201910851365.8 (15 pages).

* cited by examiner

PACKAGING HAVING SLIDING LAYER AND METHOD FOR PHARMACEUTICAL AND COSMETIC SUBSTANCES AND PREPARATION FOR PRODUCING SAME

BACKGROUND OF THE INVENTION

1. Field of the Invention

The present invention relates generally to containers for receiving pharmaceuticals and cosmetic preparations. In particular, the present invention relates to containers of this type having a sliding layer which facilitates sliding of a plunger, or stopper, for emptying the container.

2. Description of the Related Art

Plastics-based cosmetics and pharmaceuticals packagings have been prior art for several decades, but are also accompanied by various challenges. When used as pharmaceuticals packaging for syringe applications, the most significant challenge is that of moving an inserted stopper with little force. Low static and sliding friction of the stopper has the effect that the contents can be completely and speedily pressed out of the syringe, and discomfort for the patient to be treated, which may arise due to non-uniform movement of the stopper or even stalling of the stopper, is reduced to a minimum.

Primarily siliconized pharmaceuticals packagings are disclosed in the prior art for solving this challenge.

U.S. Pat. No. 4,767,414 A describes the application of silicone oil to the inner wall, after the plastics inner surface has been activated with a plasma. It would in any case be desirable to be able to dispense with the additional step of plasma activation. Moreover, chemically noncovalently bonded silicone oil may possibly find its way into the patient, in particular into the human bloodstream.

European Patent EP 0920879 B1 describes a silicone-based mixture. The mixture of a reactive silicone oil and an unreactive silicone oil enables the bonding of the silicone layer to the substrate and a good sliding property of the stopper.

A further challenge is additionally that of maintaining the sliding properties of a sliding layer during various actions on the packaging.

What is needed in the art is a container for pharmaceuticals and cosmetics that has a sliding layer that is as insensitive as possible with respect to external influences.

SUMMARY OF THE INVENTION

Exemplary embodiments provided according to the present invention provide a preparation that can be used to prepare hollow bodies with low coefficients of friction.

In some exemplary embodiments provided according to the present invention, a preparation for application to an inner side of a hollow body to produce a sliding film or a sliding layer on a packaging for pharmaceuticals or cosmetic products is provided. The liquid preparation includes: a reactive silicone system for forming a silicone network of the sliding layer; a catalyst for catalyzing the cross-linking reaction of the reactive silicone system; at least one unreactive silicone oil, such as polydimethylsiloxane; and at least one diluent. The diluent comprises a silicon-containing compound and a content of the diluent in the preparation amounts to more than 45 percent by weight and less than 95 percent by weight in the preparation.

In some exemplary embodiments provided according to the present invention, a method for producing a packaging for pharmaceuticals or cosmetic products includes applying the preparation as a layer to the inner side of the hollow body of the packaging and then the reaction of the components of the silicone multicomponent system is initiated, with the result that a silicone network forms and a solidified sliding layer is obtained.

In some exemplary embodiments provided according to the present invention, a packaging for pharmaceuticals or cosmetic products includes a cylindrical hollow body that is coated on an inner side with a sliding layer. The sliding layer has a silicone network in which a silicone oil is incorporated. The hollow body is configured such that a stopper can be introduced into the hollow body and the coefficient of static friction of the friction of a stopper, inserted into the hollow body, on the sliding layer is at most 20% greater than the average coefficient of sliding friction.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
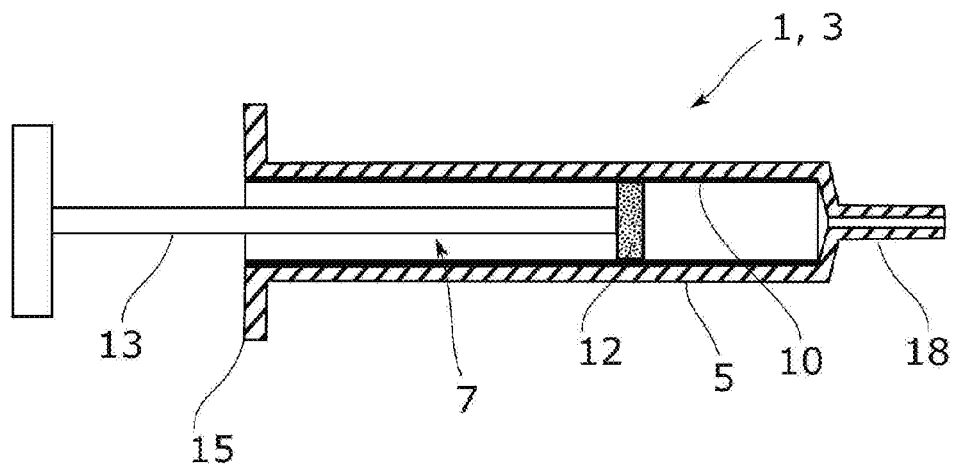
FIG. 1 illustrates a packaging for pharmaceutical or cosmetic products in the form of a syringe.

In the context of the present invention, an unreactive silicone oil is understood to mean a polysiloxane without cross-linkable or polymerizable groups. The unreactive silicone oils are especially polysiloxanes having aliphatic radicals, for example polydimethylsiloxane.

It has been found that the sliding layer becomes particularly resistant when the solvent proportion, that is to say the proportion of the diluent, amounts to more than 45 percent by weight of the preparation. Thus, for hexamethyldisiloxane (HMDSO) as diluent, a solvent proportion of at least 50 percent by weight (wt %) was observed to be favorable. Reducing the solvent proportion leads successively to less-cured layers. A greater layer strength and better curing would be expected per se for low solvent proportions, as the inclusion of solvent molecules in the polymerization chains is prevented. However, this was not the case.

According to the present invention, the diluent/the solvent comprises a silicon-containing compound. It has surprisingly been found that the Si content of the diluent plays a decisive role in layer adhesion and curing. The use of siloxanes or polysiloxanes such as for example HMDSO has been found to be advantageous here. The corresponding layers in this case have a homogeneous composition and good layer adhesion to the substrate. The good layer adhesion is especially surprising in this respect since the substrates comprise organic plastic and generally do not have any Si—O bonds that could take part in covalent interactions with the silicone oils present in the preparation and thus could achieve increased layer adhesion. It can therefore be surmised, without being restricted to this hypothesis, that the silicon-containing diluent also functions as a kind of adhesion promoter between the generally silicon-free substrate and the silicone oils in the preparation.

Siloxane-based silicon-containing diluents, such as for example HMDSO, moreover have relatively low surface tensions, which is advantageous with respect to wetting of the substrate surface. In general, and without restriction to siloxane-based diluents, in some embodiments the silicon-containing diluent has a surface tension of less than 19 mN/m.

It is moreover believed that the silicon or siloxane functionalities of the diluent have an advantageous influence on the solubility of the silicone oils in the diluent and thus also on the homogeneous dispersion of the silicone oils in the preparation, which in turn permits high homogeneity of the corresponding coating.

In contrast to this, homogeneous layers could not be obtained from preparations having silicon-free solvents such as, for example, toluene as diluent. In this case, the layer properties could not be significantly improved by increasing the diluent content either.

Conversely, yet higher proportions of the diluent in the preparation provided according to the present invention have been found to be advantageous in relation to the layer properties of the corresponding layer. It is therefore provided in a development that the diluent in the preparation amounts to a proportion of at least 60 percent by weight, such as more than 70 percent by weight, more than 80 percent by weight, or more than 82 percent by weight. The diluent of the preparation can therefore readily, and with very good properties of the sliding layer produced therefrom, take up more than $4/5$ of the total weight. In some embodiments, the content of the diluent in the mixture is 45 wt.-% or more and 95 wt.-% or less, such as: more than 45 wt.-% and less than 95 wt.-%; 50 wt.-% or more and less than 95 wt.-%; 55 wt.-% or more and less than 95 wt.-%; 60 wt.-% or more and less than 95 wt.-%; 70 wt.-% or more and less than 95 wt.-%; 75 wt.-% or more and less than 95 wt.-%; 80 wt.-% or more and 90 wt.-% or less; or 83 wt.-% or more and 88 wt.-% or less.

A low layer strength generally leads to failure of the sliding layer, since the latter is then detached by the stopper when moving in the hollow body or can even detach from the inner wall without external action of force. The desired coefficients of static and sliding friction ("SSF coefficients") can then generally not be achieved. As an example, it appears that, with an excessively low content of HMDSO as diluent, the polymerization of the reaction solution is reduced so greatly that on upright test specimens in the hollow body the reaction solution flows downwards and collects on the support.

In this case, the advantageous influence of a high content of diluent or solvent in the preparation on the layer strength of the cross-linked layer is surprising. Thus, low concentrations of the reactive groups generally lead to lower degrees of polymerization and thus to poorly cross-linked layers. However, when cross-linking the preparation provided according to the present invention, layers having a high degree of cross-linking and high layer strengths are surprisingly obtained despite high solvent proportions or proportions of diluent in the preparation. In some embodiments, the preparation has a viscosity at a temperature of 23° C. in the range of 0.5 to 200 mPas, such as 1 to 50 mPas or in the range of 1 to 10 mPas.

A diluent within the context of the present invention may be an Si-containing solvent in which the reactive silicone system and the unreactive silicone oil are soluble. In order to ensure good solubility of the silicone components of the preparation, nonpolar solvents can be used as diluents. In this case, the use of silicon-organic compounds having at most 6 silicon atoms as diluent has been found to be advantageous.

Exemplary diluents are:
cyclic silicones, such as: octamethylcyclotetrasiloxane, decamethylcyclopentasiloxane, dodecamethylcyclohexasiloxane, tetramethylcyclotetrasiloxane, pentamethylcyclopentasiloxane,
hexamethyldisiloxane (HMDSO),
octamethyltrisiloxane,
decamethyltetrasiloxane.

A mixture, especially comprising one or more of the abovementioned substances, may also be used as diluent.

The reactive silicone system for forming a silicone network has polysiloxanes having cross-linkable groups. The reactive silicone system may be a multicomponent system, such as a two-component system. Both high-temperature cross-linking (HTV systems) and low-temperature or room-temperature cross-linking silicone multicomponent systems (RTV systems) have been tested and are suitable. In this case, the reactive silicone system contains functional groups that can enter into a cross-linking reaction.

The reactive silicone system may have a first component and a second component. The first component has at least one first functional group and the second component has a plurality of second functional groups. First and second functional groups react with one another to form a common bond. The first and second functional groups can exhibit a different or else the same chemical form. For example, both the first and the second functional groups can be vinyl groups.

In some embodiments, the proportion of the first component in the reactive silicone system is greater than the proportion of the second component. The mass ratio of first to second component may be, for example, 10:1 to 30:1. The first component thus forms the basis of the silicone network formed on cross-linking, while the second component functions as cross-linker.

The required amount of silicone is very defined due to the low concentration of the silicone mixture in the solution; it is possible to apply a layer having good friction properties and minimum layer thickness without applying excess silicone.

In some embodiments, the first component comprises a vinyl-functionalized polysiloxane and the second component a polysiloxane having Si—H groups. One exemplary embodiment contains, as first component, a vinyl-functionalized polydimethylsiloxane and, as second component, a copolymer having dimethylsiloxane and methylhydrosiloxane monomer units. In this case, it has been found to be advantageous to use a copolymer having the following structure:

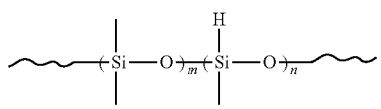

The number of cross-linking points in the sliding layer and thus the degree of cross-linking can therefore be set by the ratio m/n and the arrangement of the two monomer units in the copolymer.

The viscosity of the preparation is furthermore also influenced by the viscosity of the silicone oils contained. In some embodiments, the unreactive silicone oil has a viscosity in the range of 2,500 cSt to 50,000 cSt, such as 5,000 cSt to 35,000 cSt or 18,000 cSt to 22,000 cSt.

In some embodiments, the preparation has a viscosity at a temperature of 23° C. in the range of 1 cSt to 50000 cSt, such as 10 to 35000 cSt, 100 to 35000 cSt, 5000 to 35000 cSt, 5000 to 22000 cSt, 5000 to 18000 cSt, 5000 to 10000 cSt, 5000 to 15000 cSt, or 5000 to 5500 cSt.

The preparation also comprises a catalyst for the cross-linking reaction of the components of the silicone multicomponent system. A soluble platinum-containing catalyst, for example chloroplatinic acid, may be used.

In some embodiments, the proportion of catalyst amounts to 0.001%-5% by weight, such as 0.01%-1.5% by weight, of the reaction solution. A weight ratio of catalyst to the reactive silicone system in the range of 0.01 to 0.2, such as in the range of 0.01 to 0.1, has been found to be advantageous. In this case, the degree of polymerization or cross-linking of the sliding layer can be set by way of the catalyst proportion. At excessively low amounts of catalyst, the polymerization or cross-linking reaction proceeds only very slowly. At very high catalyst amounts, conversely, the cross-linking proceeds so rapidly that in some situations the heat of reaction released in the cross-linking reaction can no longer be dissipated and thus evaporation of the diluent occurs. The amount of diluent therefore decreases, with the result that the viscosity of the reaction solution rises. This can in turn lead to low degrees of cross-linking or polymerization due to the immobilization of the polymer chains. In this case, the corresponding sliding layer only has low stability.

In some embodiments, the preparation comprises at least one inhibitor for preventing a spontaneous reaction of the reactive silicone system. This facilitates handling of the preparation up to application of the sliding layer. In addition, the inhibitor has not proved disadvantageous for the sliding properties and the strength of the layer. In particular, organic compounds having a triple bond have been found to be suitable inhibitors. The inhibitor here can enter into reversible complex formation with the catalyst, with the result that a spontaneous cross-linking reaction of the reactive silicone system is prevented.

The present invention also relates to a method for producing the packaging. According to this method, the preparation is applied as a layer to the inner side of the hollow body and then the reaction of the components of the silicone multicomponent system is initiated, with the result that a silicone network forms and a solidified sliding layer is obtained.

The preparation can be applied in this case by simple application processes such as spraying or wiping onto the container inner wall.

The curing, i.e. the cross-linking, may be performed by heating the applied layer to temperatures in the range of 150 to 280° C. The thermal treatment can be performed in particular by way of infrared radiation or convection currents. The cross-linking reaction takes place in the reactive silicone oil system as a result of the thermal treatment. At least partial evaporation of the diluent occurs at the same time. Alternatively, the curing can also be performed by way of a plasma at markedly lower temperatures.

Durable sliding layers or sliding films are obtained in particular when the layer thickness of the sliding layer is less than 3 µm. Layer thicknesses of less than 1 µm may be provided. In order for a sufficient reserve of silicone oil to be able to be stored in the layer and for the layer to cover the intended sliding surface without interruption, it is additionally advantageous for the layer thickness to be at least 0.4 µm, such as at least 0.5 µm. The corresponding sliding layers here have high mechanical stability. Moreover, the sliding layers exhibit high resistance to water and chemicals such as ethanol or cleaning agents. In the context of the present invention, "high resistance" is understood especially to mean that the sliding friction does not, or at least does not permanently, rise after treatment of the sliding layer with the above-described substances.

It has surprisingly been found that the hollow body produced by the method provided according to the present invention can at least partially regenerate its static/sliding friction properties again on cleaning of the sliding layer. Thus, after cleaning of the sliding layer, the original static/sliding friction can be at least partially restored by storage, for example under the action of heat, for example directly prior to placing the stopper or filling. The packaging provided according to the present invention therefore has a regeneration property.

Sliding layers produced by the method provided according to the present invention, or with the preparation described herein, thus have, in addition to very low coefficients of static and sliding friction, the particular property of being able to regenerate the layer with regard to the sliding effect if the surface of the sliding layer is cleaned or in general if the unreactive silicone that contributes substantially to the sliding effect is removed from the surface.

The regeneration property can be demonstrated by cleaning the layer surface with ethyl acetate. The SSF coefficients are determined before and after the cleaning and optionally after regenerative treatment (for example storage, optionally at elevated temperature).

The present invention furthermore also relates to a packaging for pharmaceuticals or cosmetic products which comprises a cylindrical hollow body that is coated on the inner side with a sliding layer, wherein the sliding layer has a silicone network in which a silicone oil is incorporated, wherein the hollow body is configured such that a stopper can be introduced into the hollow body and the coefficient of static friction of the friction of a stopper, inserted into the hollow body, on the sliding layer is at most 20% greater, such as at most 10% greater or at most 5% greater, than the average coefficient of sliding friction. Thus, in these sliding layers the coefficients of static and sliding friction are virtually identical, whereas systems according to the prior art have markedly higher coefficients of static friction, compared to the average sliding friction, in relation to the coefficient of sliding friction. This can, for example, lead to stoppers that are moved on the sliding layer not experiencing uniform movement, and instead being inserted in an uncontrolled and rapid manner after overcoming the static friction. The packaging provided according to the present invention on the contrary enables a very uniform and controlled movement of the stopper through the hollow body.

The coefficients of static and sliding friction are ascertained by moving a suitable stopper, immediately after insertion into the hollow body, at a constant speed of 100 mm/min through the hollow body and measuring the force required for this as a function of the insertion depth. Typical static/sliding friction diagrams have a linear rise in force at the start of movement of the stopper. As soon as the force of static friction has been overcome, the stopper begins to move and there is sliding of the stopper through the cylinder which, in the case of a good sliding layer, requires a relatively constant pushing force. Immediately prior to onset of the sliding movement of the stopper there is generally a maximum in the static/sliding friction diagram, which represents the coefficient of static friction. The relatively constant force during the sliding movement represents the coefficient of sliding friction. The static/sliding friction diagrams should typically be measured with a stopper that is also used as the stopper for the primary pharmaceuticals packaging and with which a corresponding leaktightness is achieved, without however requiring too great an effort.

A standard stopper may be used. In the context of this application, a "standard stopper" consists of an elastomer that is polymerized by cross-linking/vulcanization. A standard stopper may be coated with a very thin silicone layer, since stoppers are customarily vulcanized in molds that are coated with an anti-adhesion coating, for example made of silicone, for demolding purposes. A standard stopper also has a slightly larger external diameter compared to the internal diameter of the sliding plunger, and so it experiences compression in the inserted state. Therefore, the stopper, in the case of a typical internal diameter of the sliding plunger of a syringe of the "1-ml long" format of 6.5 mm, can for example have an external diameter of 6.9+/−0.1 mm.

In some embodiments, the coefficient of static friction and/or the coefficient of sliding friction on moving a standard stopper at a speed of 100 mm/min over the sliding layer is less than 10 N, such as less than 8 N or even less than 6 N.

It has been found that the packaging provided according to the present invention surprisingly has a regeneration effect. In some embodiments, the sliding layer therefore has a regeneration effect, with the result that, after removal of the silicone oil from the surface of the sliding layer, the sliding effect of the sliding layer regenerates. It is apparent that such a packaging is very advantageous if, for example, cleaning precedes filling of the packaging with the pharmaceutical or cosmetic product. In this case, in the context of the present invention, a sliding layer is designated as a sliding layer with regeneration effect especially when, after a rise in the sliding friction from an initial level to a higher level which is determined within a period of fewer than 5 minutes after cleaning to remove the silicone oil, the sliding friction drops significantly again after a regeneration period of more than 10 minutes after cleaning to remove the silicone oil. A regeneration effect is understood in this case to also mean a drop in the sliding friction after the cleaning when, after cleaning to remove the silicone oil and subsequent regeneration time, the sliding friction does not reach the initial level again, i.e. the coefficient of friction prior to cleaning to remove the silicone oil.

The sliding layer is particularly suitable for containers made of plastic, especially for containers made of polyolefin such as cyclic olefin copolymer (COC) or cyclic olefin polymer (COP). A further suitable material is glass, especially a borosilicate glass, and/or a glass of the hydrolytic class 1b according to ISO 719. Aluminosilicate glasses are a further class of suitable glasses. Silicatic glasses having a content of $Al_2O_3$ of more than 6 percent by weight are designated as aluminosilicate glasses.

Surprisingly, a durable sliding layer can be applied even to polyolefin substrates such as for example COC or COP, even though polyolefins do not contain any silicon and therefore no covalent bonding of the silicone network to the substrate via Si—Si or Si—O bonds can take place either. Without intending to be bound to this hypothesis, it has been surmised that the silicon-containing diluent fulfils the role of intermediary between the nonpolar silicon-free substrate and the silicone network. In some embodiments, the container is therefore manufactured from a silicon-free material. Surprisingly, a primer is not required in order to apply the sliding layer and durably solidify it either in the case of silicon-free materials or in the case of silicon-containing container materials such as borosilicate glass or aluminosilicate glass. In some embodiments, the preparation is applied directly to the container inner side without pretreatment with a primer and then solidified. The sliding layer can therefore be applied directly to the inner surface of the container.

In some embodiments, the roughness of a plastics surface can be reduced by the layer provided according to the present invention. The roughness of the sliding layer here is less than 40 nm, such as less than 20 nm.

Polydimethylsiloxane is particularly suitable as unreactive silicone oil. For unreactive silicone oil it is generally advantageous if the chain length of the silicone oil is not too great, as this has advantageous effects on the regeneration capability of the sliding layer. The polydimethylsiloxane has an average chain length, and accordingly an average molar mass, which is so low that it is still an oil at 23° C. room temperature, i.e. it is fluid.

The sliding surface can in particular be arranged in a syringe or carpule in order to facilitate sliding of a stopper or plunger for drawing up and/or delivering the pharmaceutical or cosmetic product. In some embodiments, provision is made for the packaging to be a syringe or carpule. The sliding layer in this case may cover at least that region of the inner side of the hollow body over which the stopper can slide.

This feature evidently results from the specific preparation with the high proportion of diluent, independently of any regeneration capability of the sliding layer after cleaning to remove the silicone oil.

In some embodiments, the sliding layers have a ratio $\mu_G/\mu_H$ of coefficient of sliding friction $\mu_G$ to the coefficient of static friction $\mu_H$ of more than 0.8. The ratio $\mu_G/\mu_H$ may be, for example, at least 0.9 or even 0.95. Thus, in these sliding layers the static friction and sliding friction are virtually identical, whereas sliding layers from the prior art have a greater static friction compared to the sliding friction. This can for example lead to stoppers that are moved on the sliding layer not experiencing uniform movement, and instead being stopped.

The present invention will be explained further herein on the basis of exemplary embodiments and the appended figures.

Exemplary Embodiment 1

In a first exemplary embodiment, 10 g of a vinyl-functionalized polydimethylsiloxane were initially charged in a reaction vessel and admixed with 65 g of decamethylcyclopentasiloxane. Under constant stirring at 800 rpm, 0.5 g of methylhydrosiloxane/dimethylsiloxane copolymer, 6.25 g of liquid polydimethylsiloxane, 0.01 g of 10% hexachloridoplatinic acid in isopropanol as catalyst and 0.05 g of 2,4,7,9-tetramethyl-5-decyne-4,7-diol as inhibitor were added to this reaction mixture. The reaction solution can be used after a stirring time of 60 s. In this case, the vinyl-functionalized polymethylsiloxane and the methylhydrosiloxane/dimethylsiloxane copolymer form the reactive silicone system, the polydimethylsiloxane forms the unreactive silicone oil and decamethylcyclopentasiloxane forms the diluent.

Figure 2:
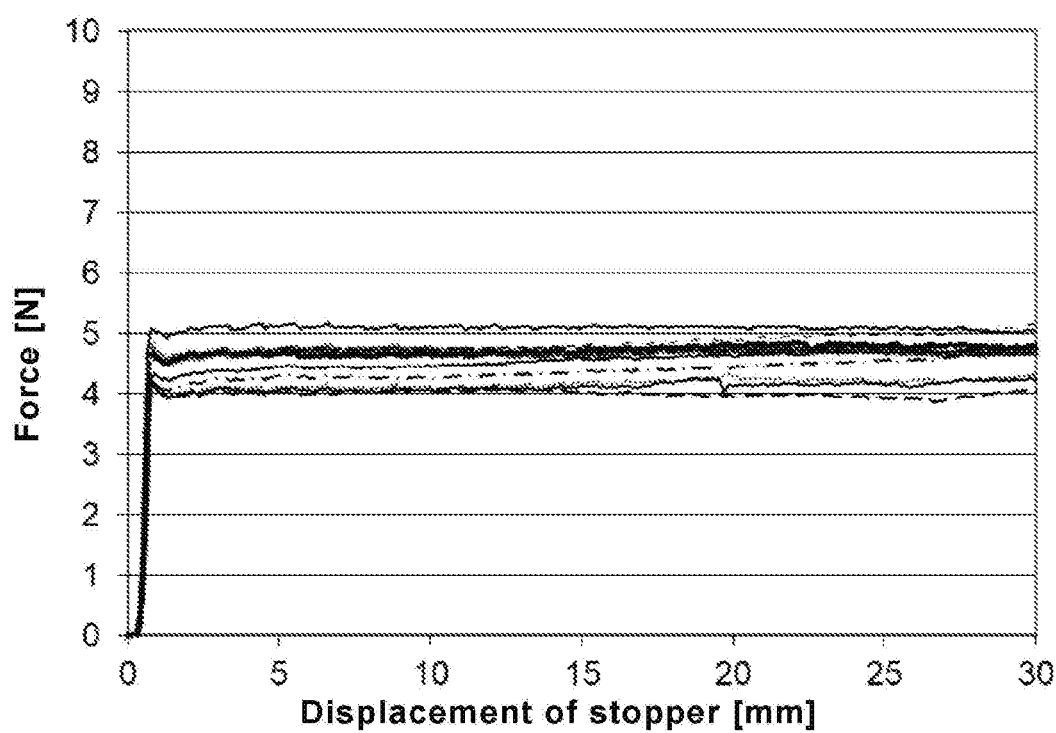
FIG. 2 illustrates a diagram with coefficients of friction for stopper displacement for ten syringes.

The preparation thus prepared was applied to the plastics hollow body on the inner side by a wiping process and cured by heating to 175° C. for 20 s. A 1-ml COC syringe of the "1-ml long" standard size with an internal diameter of 6.5 mm was used as substrate here for depositing the sliding layer. Coefficients of static and sliding friction for the cured sliding layer were subsequently determined. This involved pressing the V9361 FM457/0 FLNC2 057 stopper from Datwyler Pharma Packaging having an external diameter of 6.9+/−0.1 mm into the syringe at a speed of 100 mm/min. The forces required for this were recorded. The coefficients for both static and sliding friction were less than 10 N here. The result of the measurement is shown in FIG. 2.

Exemplary Embodiment 2

In a second exemplary embodiment, 80 g of a vinyl-functionalized polydimethylsiloxane were initially charged in a reaction vessel and admixed with 640 g of hexamethyldisiloxane. Under constant stirring at 1000 rpm, 2 g of methylhydrosiloxane/dimethylsiloxane copolymer, 48 g of liquid polydimethylsiloxane, 1.1 g of 1,1,3,3-tetramethyl-1,3-divinyldisiloxane-complexed platinum and 0.1 g of butynol as inhibitor were added to this reaction mixture. The preparation can be used after a stirring time of 60 s.

The preparation was applied to the plastics hollow body on the inner side by a wiping process and cured by heating to 250° C. for 3.5 s. A 1-ml COC syringe of the "1-ml long" standard size with an internal diameter of 6.5 mm was used as substrate here for depositing the sliding layer. Coefficients of static and sliding friction for the cured sliding layer were subsequently determined. This involved pressing the V9361 FM457/0 FLNC2 057 stopper from Datwyler Pharma Packaging having an external diameter of 6.9+/−0.1 mm into the syringe at a speed of 100 mm/min. The forces required for this were recorded. The coefficients for both static and sliding friction were less than 10 N here.

Table 1 illustrates the roughness values of an uncoated syringe made from COC and the roughness of the surface of the corresponding syringe after applying a sliding layer provided according to the present invention.

TABLE 1

Comparison of roughness values

| Test specimen | Region | Rms nm | Ra nm |
|---|---|---|---|
| coated COC syringe, 20 ml | near taper | 10 | 7 |
| | middle | 12 | 9 |
| non-sterile uncoated COC syringe, 20 ml | near flange | 29 | 24 |
| | near taper | 19 | 14 |
| | middle | 40 | 27 |
| | near flange | 79 | 62 |

The roughness values were determined according to DIN EN ISO/IEC 17025 using a white-light interferometer.

Exemplary Embodiment 3

In a third exemplary embodiment, 80 g of a vinyl-functionalized polydimethylsiloxane were initially charged in a reaction vessel and admixed with 640 g of decamethylcyclopentasiloxane. Under constant stirring at 1000 rpm, 2 g of methylhydrosiloxane/dimethylsiloxane copolymer, 48 g of liquid polydimethylsiloxane, 1.1 g of 10% hexachloridoplatinic acid in isopropanol as catalyst and 0.1 g of butynol as inhibitor were added to this reaction mixture. The preparation can be used after a stirring time of 60 s.

The preparation was applied to the plastics hollow body on the inner side by a wiping process and cured by heating to 250° C. for 3.5 s. A 1-ml COC syringe of the "1-ml long" standard size with an internal diameter of 6.5 mm was used as substrate here for depositing the sliding layer. Coefficients of static and sliding friction for the cured sliding layer were subsequently determined. This involved pressing the V9361 FM457/0 FLNC2 057 stopper from Datwyler Pharma Packaging having an external diameter of 6.9+/−0.1 mm into the syringe at a speed of 100 mm/min. The forces required for this were recorded. The coefficients for both static and sliding friction were less than 10 N here.

The sliding layer provided according to the present invention has a low roughness. In some embodiments, the roughness Rms of the sliding layer is at most 40 nm, such as at most 30 nm or at most 20 nm. Particularly low coefficients of static and sliding friction can be achieved by way of the low roughness. In some embodiments, the roughness of the substrates used can moreover be reduced by applying a sliding layer provided according to the present invention. This is advantageous when using plastics substrates such as for example COC substrates which have a higher roughness compared to glass. In some embodiments, a substrate coated with the sliding layer provided according to the present invention has a roughness Rms that is reduced compared to the corresponding uncoated substrate by at least 20%, such as at least 40%.

The influence of the individual components on the properties of the preparation or sliding layer will be demonstrated further herein on the basis of comparative examples.

Comparative Example 1: Influence of the Diluent Content 80 g of a vinyl-functionalized polydimethylsiloxane were initially charged in a reaction vessel and admixed with 80 g of hexamethyldisiloxane. Under constant stirring at 400 rpm, 2 g of methylhydrosiloxane/dimethylsiloxane copolymer, 48 g of liquid polydimethylsiloxane, 1.1 g of 10% hexachloridoplatinic acid in isopropanol as catalyst and 0.1 g of butynol as inhibitor were added to this reaction mixture. The reaction solution can be used after a stirring time of 60 s.

The reaction solution was applied to the plastics hollow body on the inner side by means of a wiping process and an attempt was made to cure it by means of heating to 250° C. for 3.5 s.

The reaction solution did not, however, remain completely in the plastics hollow body when stored upright with the opening facing downwards or it collected at the bottom in the plastics hollow body when stored horizontally. On account of the high inhomogeneity of the layer in the plastics hollow body, measurement of the coefficient of static or sliding friction was dispensed with.

Comparative Example 2 (Influence of the Diluent)

In this comparative example, toluene was used as diluent, which stands out among the diluents due to its nonpolar nature without containing Si atoms. Thus, 80 g of a vinyl-functionalized polydimethylsiloxane were initially charged in a reaction vessel and admixed with 640 g of toluene. Under constant stirring at 400 rpm, 2 g of methylhydrosiloxane/dimethylsiloxane copolymer, 48 g of liquid polydimethylsiloxane, 1.1 g of 1,1,3,3-tetramethyl-1,3-divinyldisiloxane-complexed platinum as catalyst and 0.1 g of butynol as inhibitor were added to this reaction mixture. The reaction solution can be used after a stirring time of 60 s.

The preparation was applied to the plastics hollow body on the inner side by a wiping process and an attempt was made to cure it by heating to 250° C. for 3.5 s.

The preparation exhibited severe wetting defects and did not form any homogeneous film. Severe droplet formation was visible. The reaction solution did not cure completely. On account of the high inhomogeneity of the layer in the plastics hollow body, measurement of the coefficient of static or sliding friction was dispensed with. It thus becomes clear that the diluent cannot be selected merely with respect to its compatibility, that is to say the solubility of the individual preparation components.

Comparative Example 3 (Influence of the Diluent)

Comparable results were also obtained with the third comparative example.

80 g of a vinyl-functionalized polydimethylsiloxane were initially charged in a reaction vessel and admixed with 640 g of cyclohexane. Under constant stirring at 400 rpm, 2 g of methylhydrosiloxane/dimethylsiloxane copolymer, 48 g of liquid polydimethylsiloxane, 1.1 g of 1,1,3,3-tetramethyl-1,3-divinyldisiloxane-complexed platinum as catalyst were added to this reaction mixture.

The reaction solution was applied to the plastics hollow body on the inner side by a wiping process and an attempt was made to cure it by heating to 250° C. for 3.5 s.

The reaction solution exhibited severe wetting defects and did not form any homogeneous film. Droplet and streak formation could be observed. The reaction solution did not cure completely. On account of the high inhomogeneity of the layer in the plastics hollow body, measurement of the coefficient of static or sliding friction was dispensed with.

Comparative Example 4 (Catalyst Amount)

80 g of a vinyl-functionalized polydimethylsiloxane were initially charged in a reaction vessel and admixed with 640 g of toluene. Under constant stirring at 400 rpm, 2 g of methylhydrosiloxane/dimethylsiloxane copolymer, 48 g of liquid polydimethylsiloxane, 11 g of 1,1,3,3-tetramethyl-1,3-divinyldisiloxane-complexed platinum as catalyst were added to this reaction mixture. The proportion of the catalyst in this comparative example amounts to 1.4% by weight. The ratio between the weight of the catalyst and the weight of the reactive silicone system is 1:7.45.

On account of the greatly increased proportion of catalyst, the preparation exhibited a strongly exothermic reaction with the formation of gases. It can be surmised here that this was gaseous toluene. The preparation gelled and application of a film was not possible.

Referring now to the drawings, FIG. 1 illustrates a packaging 1 in an exemplary embodiment provided according to the present invention as a syringe 3 for administering pharmaceuticals or cosmetics. The syringe 3 is made, for example, of glass or of plastic and is a hollow body 5 having a cylindrical portion 7 and a Luer taper 18 onto which, for example, an injection needle can be placed. A stopper 12 is inserted in the cylindrical portion and is displaceable in the axial direction by pressure on a push rod 13. The cylindrical portion has a flange 15 for handling purposes at the end of the introduction opening for the stopper 12.

The packaging 1 is provided with a sliding layer 10 on an inner side, here specifically on the inner side of the cylindrical portion 7. The sliding layer thus covers that region of the inner side of the hollow body 5 over which the stopper 12 can slide when the syringe is being emptied or used for drawing up.

The sliding layer 10 is embodied as a silicone network in which a silicone oil is incorporated.

A sliding layer 10, as can be produced with the preparation described herein and by the method, is generally also distinguished by the fact that the coefficients of friction on moving the stopper are not only low, but also very uniform. This relates both to the variation of the coefficients of friction along the displacement path of the stopper and to the differences between different packagings.

This is supported by the diagram of FIG. 2. The diagram illustrates the coefficients of friction on moving the stopper for ten different syringes. The frictional force was recorded for the whole of the possible displacement path. For measuring the static/sliding friction curves, a stopper was inserted into the syringe and then the static/sliding friction curve was recorded. As illustrated, the fluctuations between the various tested specimens are at most approximately one newton, wherein tolerances in the material and the dimensions of the stopper contribute substantially here, too. It is additionally apparent from FIG. 2 that all syringes measured have a ratio $\mu_G/\mu_H$ of the coefficients of friction of more than 0.95. The results are summarized in Table 2.

TABLE 2

| Coefficients of static and sliding friction of the measurements illustrated in FIG. 2 | | | |
|---|---|---|---|
| Test specimen | $F_{sliding\ friction}$ [N] | $F_{static\ friction}$max [N] | $\mu_G/\mu_H$ |
| 1 | 4.49 | 4.33 | 1.03 |
| 2 | 4.13 | 4.20 | 0.98 |
| 3 | 4.26 | 4.36 | 0.98 |
| 4 | 4.73 | 4.53 | 0.96 |
| 5 | 4.62 | 4.73 | 0.98 |
| 6 | 4.22 | 4.41 | 0.96 |
| 7 | 4.87 | 4.61 | 1.06 |
| 8 | 4.34 | 4.24 | 1.02 |

TABLE 2-continued

Coefficients of static and sliding friction
of the measurements illustrated in FIG. 2

| Test specimen | $F_{sliding\ friction}$ [N] | $F_{static\ friction}$max [N] | $\mu_G/\mu_H$ |
|---|---|---|---|
| 9 | 4.04 | 4.28 | 0.94 |
| 10 | 5.19 | 4.85 | 1.07 |

Here, the ratio $\mu_G/\mu_H$ can be read directly from the coefficients of friction listed in Table 2. Thus, the force measured immediately at the start of the displacement procedure of the stopper can be attributed to the static friction, the average sliding friction can be assigned to the force measured during the displacement procedure. The force $F_{sliding\ friction}$ listed in Table 2 here provides the value for the sliding friction averaged over all measured values obtained during displacement of the stopper in the region from 3 to 30 mm. By dividing the two force values the ratio $\mu_G/\mu_H$ can thus be ascertained.

The fluctuations along the displacement path are in each case considerably lower still if only a single syringe is considered. In all cases, the sliding friction fluctuates by less than 0.5 newton along the path. This is advantageous for ensuring uniform movement and uniform effort when delivering the contents of the packaging. The sliding friction in the examples shown is between 4 newtons and 5 newtons. Although the absolute magnitude of the frictional force also depends on the dimensions, the relative fluctuation is a variable that is substantially independent thereof. Without being restricted to the specifically illustrated exemplary embodiment, provision is made to this end according to some embodiments for the friction along the displaceable path of the stopper to fluctuate by at most one-tenth of the average value of the friction.

It is also striking that the curves at the start of the displacement exhibit virtually no overshoot due to increased static friction.

Figure 3:
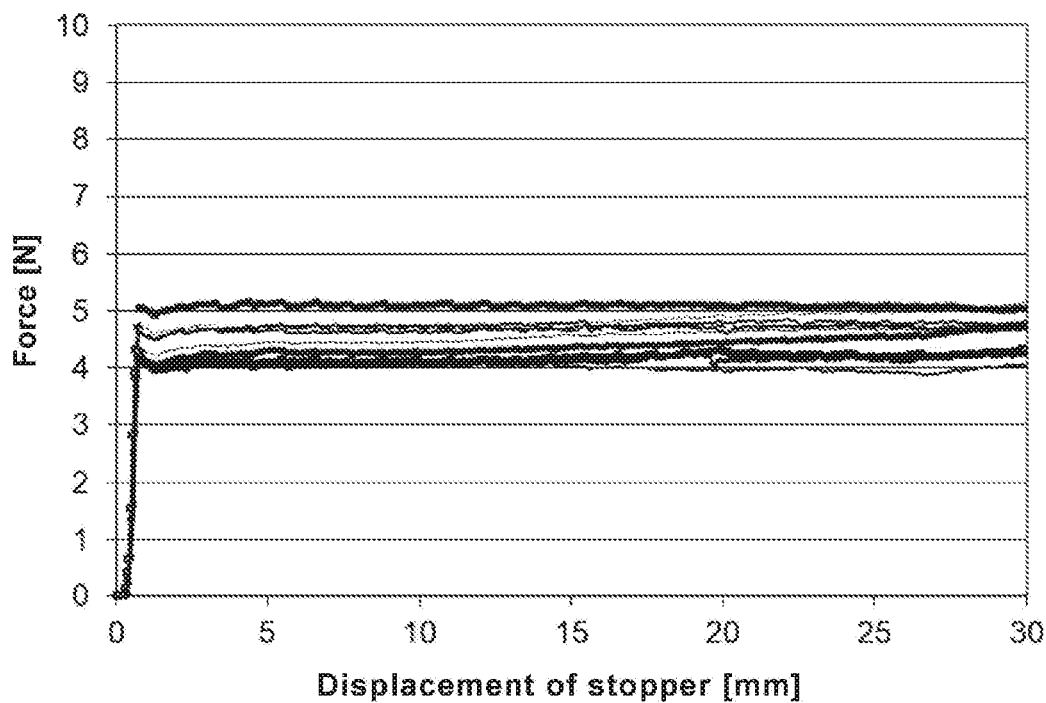
FIG. 3 illustrates a diagram with coefficients of friction for stopper displacement after treating the syringe for 60 s in water using ultrasound.

A sliding layer produced with the preparation also proves to be resistant to various handling operations of the interior space of the hollow body. The diagram in FIG. 3 illustrates an example of this. As with FIG. 2, the diagram illustrates measured values of the frictional force on displacing the stopper on the sliding layer along the syringe. Once again, ten specimens were measured. The syringes were subjected to ultrasound treatment in water for 60 seconds prior to the measurement. Comparison with the measured values of FIG. 2 illustrates that the friction is not influenced, in particular that the friction does not noticeably increase after the ultrasound treatment.

Figure 4:
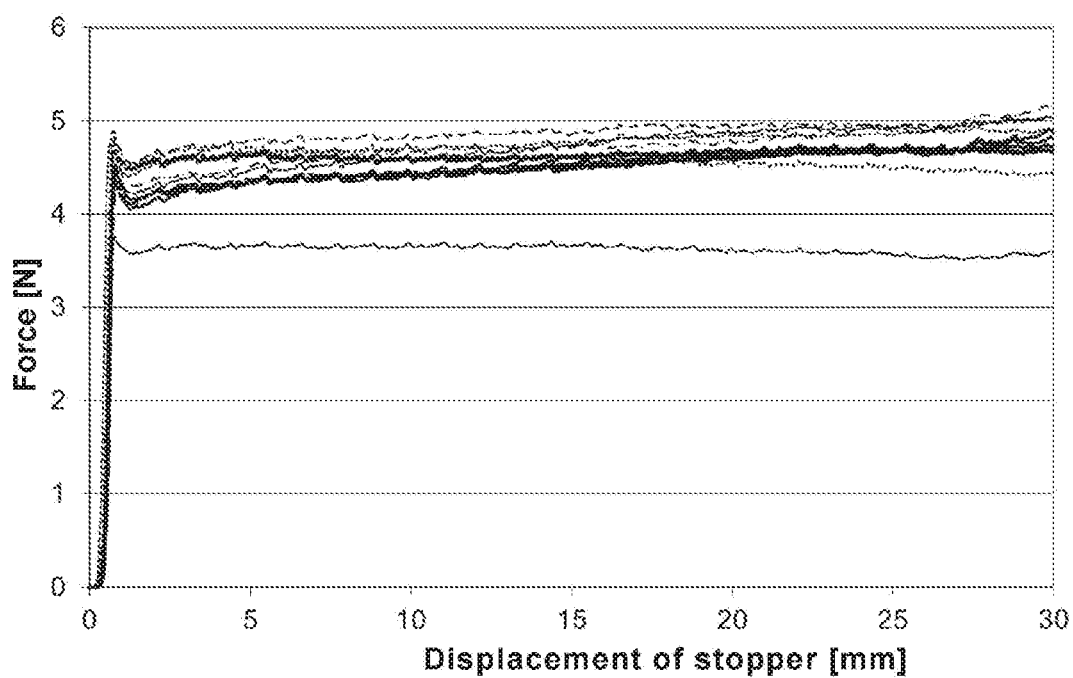
FIG. 4 illustrates a diagram with coefficients of friction for stopper displacement after treating the syringe for 60 s in a 0.1 M aqueous NaOH solution, the storage time before measurement was 30 min.

FIG. 4 analogously illustrates the measured values of the frictional force on displacing the stopper on the sliding layer after ultrasound treatment of the measured syringes for 60 s in a 0.1 M aqueous NaOH solution. Here, too, the friction is barely influenced, which indicates a high stability of the sliding layer even with respect to high pH.

Figure 5:
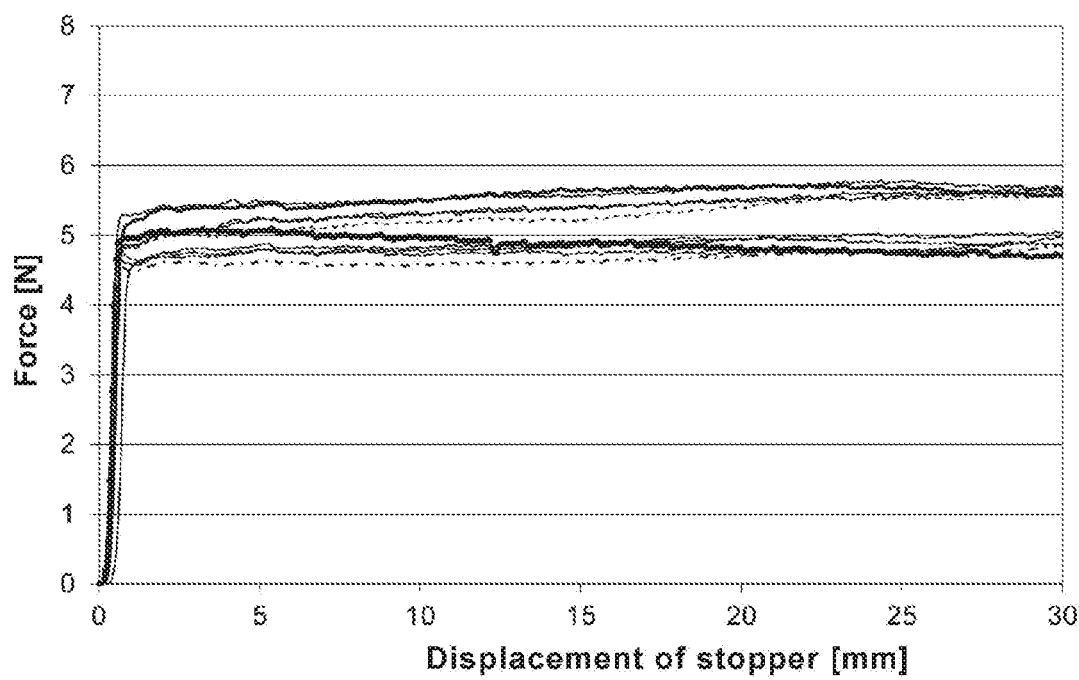
FIG. 5 illustrates a diagram with coefficients of friction for stopper displacement after treating the syringe for 60 s in acetone using ultrasound.

FIG. 5 illustrates the measured values of the frictional force on displacing the stopper on the sliding layer after ultrasound treatment of the corresponding syringe in acetone for 60 s. The friction is barely influenced by the treatment, which speaks to a high resistance of the sliding layer with respect to polar organic solvents.

Figure 6:
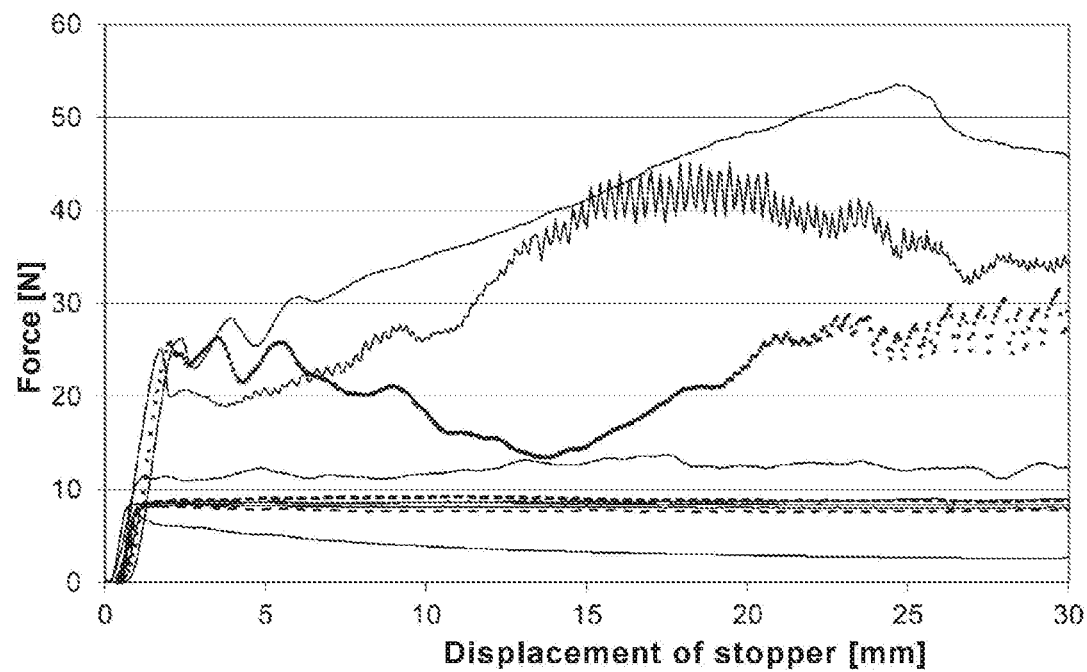
FIG. 6 illustrates a diagram with coefficients of friction for stopper displacement after removing the unreactive silicone oil from the sliding layer (via 60 s of ultrasound treatment with ethyl acetate)
Figure 7:
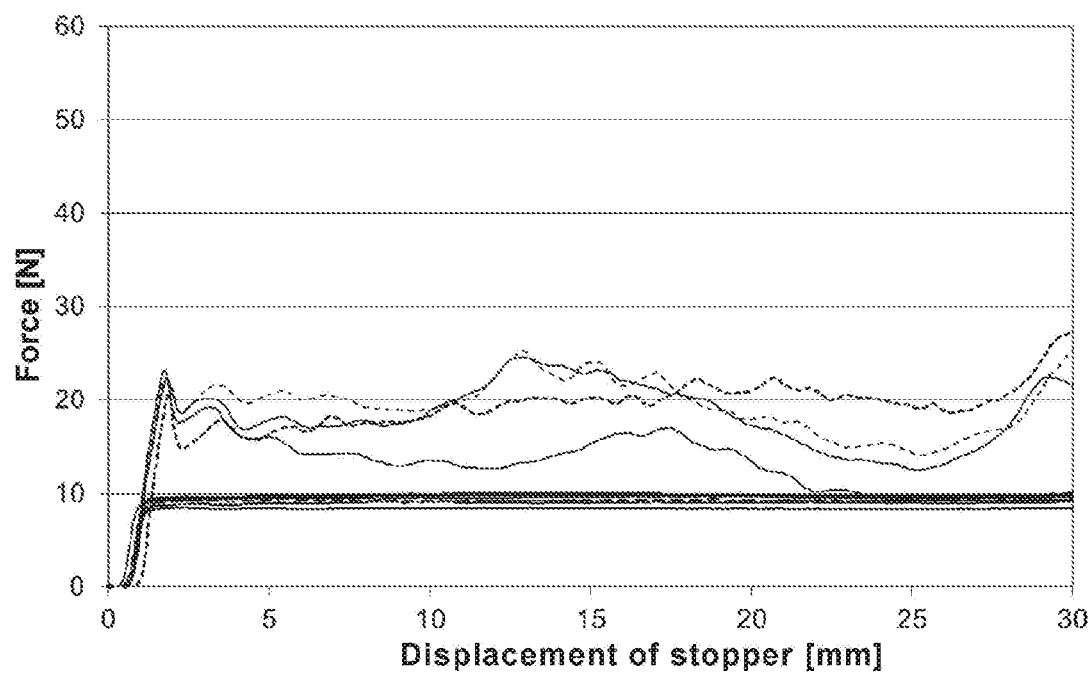
FIG. 7 illustrates a diagram with coefficients of friction for stopper displacement after removing the unreactive silicone oil from the sliding layer and subsequently storing for 24 h at room temperature.
Figure 8:
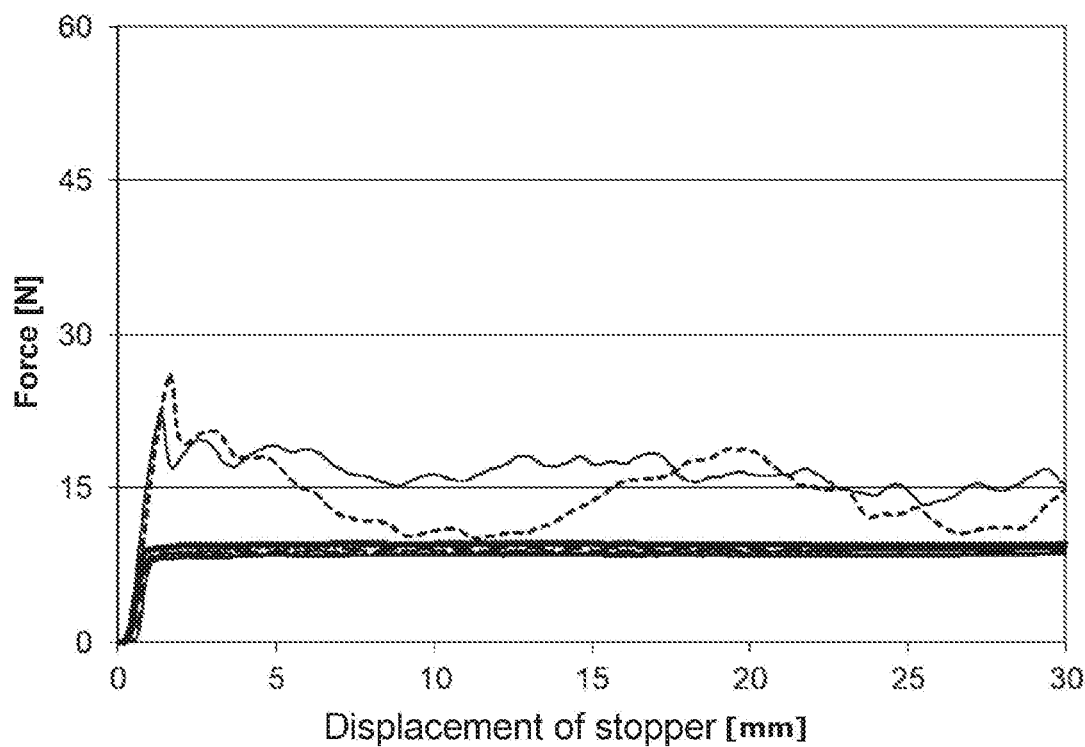
FIG. 8 illustrates a diagram with coefficients of friction for stopper displacement after removing the unreactive silicone oil from the sliding layer and subsequently storing for 24 h at 40° C.

FIGS. 6 to 8 show the regeneration capability of the sliding layers provided according to the present invention. The regeneration property is tested in this case by cleaning the layer surface with ethyl acetate (for 60 s in ultrasound). The SSF coefficients are taken after cleaning (FIG. 6) and possibly after regenerative treatment (e.g. storing, possibly at elevated temperature, FIG. 7 and FIG. 8).

It has surprisingly been found that the plastics hollow body produced by the method provided according to the present invention can at least partially regenerate its static/sliding friction properties again on cleaning of the sliding layer. While measurement immediately after the cleaning (FIG. 6) illustrates markedly higher SSF coefficients, the original static/sliding friction can be at least partially restored by storage. This can be shown using FIG. 7. The syringe thus has a regeneration property.

It is apparent from FIG. 8 that slightly elevated temperatures are advantageous for this.

If, in contrast, the silicone network is to a large extent destroyed by mechanical actions, for example by cleaning with a pipe cleaner, a regenerative effect can no longer be observed.

The compositions of additional preparations A, B, C, D, and E are described in Table 3. In the columns of Table 3, the substances are: 1) vinyl-functionalized polydimethylsiloxane; 2) methylhydrosiloxane-dimethylsiloxane copolymer; 3) 10% hexachloridoplatinacid in isopropanol; 4) liquid polydimethylsiloxane; and 5) hexamethyldisiloxane (HMDSO).

TABLE 3

Wt-% compositions of preparations A, B, C, D, and E

| name | 1 [wt.-%] | 2 [wt.-%] | 3 [wt.-%] | 4 [wt.-%] | 5 [wt.-%] |
|---|---|---|---|---|---|
| A | 41.69 | 1.04 | 0.59 | 16.68 | 40.00 |
| B | 38.22 | 0.96 | 0.54 | 15.29 | 45.00 |
| C | 10.59 | 0.26 | 0.15 | 4.24 | 84.75 |
| D | 3.47 | 0.09 | 0.05 | 1.39 | 95.00 |
| E | 0.69 | 0.02 | 0.01 | 0.28 | 99.00 |

The spreading behaviors of preparations A, B, C, D, and E are described in Table 4. The spreading behavior was observed on a purified borosilicate glass. 10 µl of each preparation was applied at RT (23° C.). The droplet size of the applied solutions was measured by a microscope. The first measurement (0 sec) was made as quickly as possible, i.e., about 1 s after application. The measurements were repeated in each case (duplicate determination).

TABLE 4

Spreading behavior of preparations A, B, C, D, and E

| name | 0 s [mm] | 5 s [mm] | 30 s [mm] | 60 s [mm] | 120 s [mm] |
|---|---|---|---|---|---|
| A | 7.0 | 7.4 | 8.1 | 8.3 | 8.4 |
| B | 7.5 | 7.9 | 8.8 | 9.0 | 9.0 |
| C | 12.2 | 12.4 | 13.1 | 13.0 | 13.2 |
| D | 7.3 | 7.5 | 7.6 | 7.5 | 7.6 |
| E | 7.8 | 7.2 | 3.4 | N/A* | N/A* |

*incapable of measurement, since a huge amount is evaporated

In some embodiments, the spreading of 10 µL of a preparation provided according to the present invention on a cleaned glass surface after about 5 seconds is 7.3 mm or more and 20 mm or less, such as: 7.5 mm or more and 18 mm or less; 7.9 mm or more and 17 mm or less; 9.0 mm or more and 16 mm or less; 9.5 mm or more and 15 mm or less; 10.0 mm or more and 14 mm or less; 11.0 mm or more and 13.5 mm or less; or 12.0 mm or more and 13.0 mm or less, Contact angle measurements of preparations A, B, C, D, and E are described in Table 5. To measure the contact angles, drop shape analysis was used. Drop shape analysis (DSA) is an image analysis method for determining the contact angle from the shape of a lying drop. For this purpose, a drop at 23° C. was applied to a cleaned borosilicate glass (lying drops). With the help of a camera, a picture of the drop was taken and transferred to the drop shape analysis DSA software. On the basis of a grayscale analysis of the image, a contour recognition was first performed. In the second step, a geometrical model describing the drop shape was fitted to the contour. From this, the angle between the drop shape and the sample surface was determined (=contact angle). Droplet shape analysis was performed within 3 seconds of application of the drop and repeated at least two times. The measurement started immediately after the drop has formed.

TABLE 5

Contact angles of preparations A, B, C, D, and E

| Name | 0 s [°] | 1 s [°] | 2 s [°] | 3 s [°] |
|---|---|---|---|---|
| A | 48.5 | 28 | 21 | 17 |
| B | 48 | 22.75 | 18.25 | 16 |
| C | <5 | <5 | <5 | <5 |
| D | <5 | <5 | <5 | <5 |
| E | <5 | <5 | <5 | <5 |

In some embodiments, the contact angle of a preparation provided according to the present invention after about one second is less than 28°, such as less than 26°, less than 24°, less than 22°, less than 20°, less than 18°, less than 15°, less than 12°, less than 10°, or less than 5°.

When the diluent concentration is 45% by weight or more, the contact angle quickly becomes smaller. The mixture wets the surface faster with a diluent concentration of 45% or higher. As previously described in the Examples, the wetting is more homogeneous at these concentrations. Formation of islands, similar to the lotus effect, does not occur at a diluent concentration of 45% or higher, which wets the surface homogeneously. The higher the diluent concentration, the higher the crosslinking speed (see Comparative Example 1) and the faster it can be applied.

If the diluent concentration is 95% by weight or less, the mixture spreads over 7 mm after 30 seconds, while if the diluent concentration is above 95%, spread is no longer measurable. If diluent concentration is within the described range, optimal spreading behavior can be observed after 5 seconds. At diluent concentrations of more than 95%, no homogeneous application is possible, the layer remaining after evaporation is too thin to reduce friction, and application is not economical because too much solvent is used that does not improve the properties and merely evaporates.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE NUMERALS 1 packaging
3 syringe
5 hollow body
7 cylindrical portion
10 sliding layer
12 stopper
13 push rod
15 flange
18 Luer taper

What is claimed is:

1. A preparation, comprising:
   a reactive silicone system comprising at least one polysiloxane having cross-linkable groups for forming a silicone network of a sliding layer;
   a catalyst for catalyzing a cross-linking reaction of the reactive silicone system;
   at least one unreactive silicone oil; and
   at least one diluent comprising a silicon-containing compound, a content of the at least one diluent in the preparation amounting to more than 45 percent by weight and less than 95 percent by weight in the preparation.

2. The preparation of claim 1, wherein the reactive silicone system is a multicomponent system comprising a first component and a second component.

3. The preparation of claim 2, wherein the first component has at least one first functional group and the second component has a plurality of second functional groups.

4. The preparation of claim 2, wherein a mass ratio of the first component to the second component is in the range of 10:1 to 30:1.

5. The preparation of claim 1, wherein the preparation has a viscosity at a temperature of 23° C. in the range of 1 cSt to 50,000 cSt.

6. The preparation of claim 1, wherein the at least one diluent at least one of comprises a silicon-containing organic compound having at most 6 silicon atoms or has a surface tension of less than 19 mN/m.

7. The preparation of claim 6, wherein the at least one diluent comprises at least one of the following diluents: cyclic silicone, octamethylcyclotetrasiloxane, decamethylcyclopentasiloxane, dodecamethylcyclohexasiloxane, tetramethylcyclotetrasiloxane, pentamethylcyclopentasiloxane, hexamethyldisiloxane (HMDSO), octamethyltrisiloxane, or decamethyltetrasiloxane.

8. The preparation of claim 1, wherein the preparation has a viscosity at a temperature of 23° C. in the range of 0.5 to 200 mPas.

9. The preparation of claim 1, wherein the catalyst comprises at least one of an organometallic catalyst, a platinum-containing catalyst, or chloroplatinic acid.

10. The preparation of claim 9, wherein at least one of a proportion of catalyst in the preparation amounts to 0.001%-5% by weight or a weight ratio of catalyst to the reactive silicone system is in the range of 0.01 to 0.2.

11. The preparation of claim 1, wherein the preparation comprises an inhibitor for preventing a spontaneous reaction of the reactive silicone system.

12. The preparation of claim 11, wherein the inhibitor is an alkyne.

13. The preparation of claim 1, wherein the at least one silicone oil is homogeneously dispersed in the preparation.

14. The preparation of claim 1, wherein the at least one diluent amounts to at least 80 percent by weight in the preparation.

15. The preparation of claim 1, wherein the preparation is reactable to form a solidified sliding layer, wherein a coefficient of static friction of a stopper contacting the solidified sliding layer is at most 20% greater than an average coefficient of sliding friction of the stopper against the solidified sliding layer.

16. The preparation of claim 1, wherein a sliding layer produced on a surface from the preparation is capable of regenerating after cleaning the surface or after the at least one unreactive silicone oil is removed from the surface.

17. The preparation of claim 1, wherein spreading of 10 μL of the preparation on a cleaned glass surface after about 5 seconds is 7.3 mm or more and 20 mm or less.

18. The preparation of claim 1, wherein a contact angle of the preparation on a cleaned glass surface after about one second is less than 28°.

19. A packaging for pharmaceuticals or cosmetic products, comprising:
a cylindrical hollow body that is coated on an inner side with a sliding layer, the sliding layer having a silicone network in which a silicone oil is incorporated, the hollow body being configured such that a stopper is insertable into the hollow body and a coefficient of static friction of the stopper, inserted into the hollow body, on the sliding layer is at most 20% greater than an average coefficient of sliding friction, the sliding layer being formed by reaction of a preparation, the preparation comprising:
a reactive silicone system for forming the silicone network of the sliding layer;
a catalyst for catalyzing a cross-linking reaction of the reactive silicone system;
at least one unreactive silicone oil; and
at least one diluent comprising a silicon-containing compound, a content of the at least one diluent in the preparation amounting to more than 45 percent by weight and less than 95 percent by weight in the preparation.

* * * * *